United States Patent [19]

Schirrmacher

[11] Patent Number: 5,273,745

[45] Date of Patent: Dec. 28, 1993

[54] VIRUS-MODIFIED TUMOR VACCINES FOR IMMUNOTHERAPY OF TUMOR METASTASES

[75] Inventor: Volker Schirrmacher, Unterer Fauler Pelz 6, D-6900 Heidelberg, Fed. Rep. of Germany

[73] Assignee: Volker R. Schirrmacher, Heidelberg, Fed. Rep. of Germany

[21] Appl. No.: 449,851

[22] PCT Filed: Feb. 27, 1989

[86] PCT No.: PCT/EP89/00186

§ 371 Date: Dec. 28, 1989

§ 102(e) Date: Dec. 28, 1989

[87] PCT Pub. No.: WO89/07946

PCT Pub. Date: Sep. 8, 1989

[30] Foreign Application Priority Data

Mar. 1, 1988 [DE] Fed. Rep. of Germany ....... 3806565

[51] Int. Cl.$^5$ .......................... A61K 39/12; C12N 7/00
[52] U.S. Cl. ......................................... 424/89; 424/88; 435/235.1; 435/236; 435/237; 435/239
[58] Field of Search ................. 424/89, 88; 435/235.1, 435/236, 237, 239

[56] References Cited

PUBLICATIONS

Liebrich et al., *Eur. J. Cancer*, vol. 27, No. 6, pp. 703-710, 1991.

Schirrmacher et al., in *Cancer Metastasis*, Schirrmacher et al., Eds., Springer-Verlag, Berlin, pp. 157-170, 1989.

Schirrmacher et al., *Clin. Expl. Metastasis*, vol. 5, No. 2, pp. 147-156, 1986.

"Prevention of Metastatic Spread by Postoperative Immunotherapy with Virally Modified Autologous Tumor Cells. I. Parameters for Optimal Therapeutic Effects", R. Heicappell et al., *Int. J. Cancer*, 37, 569-577 (1986).

"Modification of Tumor Cells by a Low Dose of Newcastle Disease Virus. Augmentation of the Tumor-Specific T Cell Response in the Absence of an Anti-Viral Response", Paul Von Hoegen et al., *Eur. J. Immunol.*, 18, 1159-1166 (1988).

"Natural Killer Cell Cytotoxic Potential of Patients with Ovarian Carcinoma and its Modulation with Virus-Modified Tumor Cell Extract", Eva Lotzova et al., *Cancer Immunol Immunother*, 17, 124-129 (1984).

*Primary Examiner*—Michael G. Wityshyn
*Assistant Examiner*—Abdel A. Mohamed
*Attorney, Agent, or Firm*—Venable, Baetjer, Howard & Civiletti

[57] ABSTRACT

The invention discloses a virus-modified tumour-specific vaccine consisting of corresponding separated tumour cells inactivated by irradiation and incubated with NDV (Newcastle Disease Virus) under sterile conditions in serum-free medium. The vaccine may optionally be irradiated again prior to application.

20 Claims, No Drawings

VIRUS-MODIFIED TUMOR VACCINES FOR IMMUNOTHERAPY OF TUMOR METASTASES

The invention relates to the preparation of virus-modified tumour-vaccines, and their use in immunotherapy of tumour metastases.

Even after extensive removal of the primary tumour it is still a problem to prevent the formation of metastases either due to growing out of micrometastases already present at the time of surgery, or to the formation of new metastases by tumour cells sown out during the operation.

In addition to classical chemotherapeutic approaches, more recently it has been tried to activate the patient's own immune-system such that it prevents the formation of micrometastases or eliminates metastases already formed, resp., by the formation of T killer cells which are as tumour-specific as possible. So called oncolysates, i.e. lysates of tumour cells, mostly from tumour cell-lines, have been used for the immunization of the patient with varying success. In doing this the problem arises that such cell lysates, which, in addition, are usually not isolated from the actual tumour cells, but from tumour cell-lines grown in cell culture, are not sufficiently immunogenic, and therefore do not lead to sufficient stimulation of the immune defence of the patients as to effectively prevent the formation of metastases.

It was now the object of the present invention to prepare tumour-specific vaccines improved with respect to their immunogenicity and tumour-specificity, which upon active immunization can selectively induce a specific immune response in the immune system of the patient, and thereby build a systemic immunity against tumour metastases, as well as to use such vaccines in the therapy of malignant tumours.

It can be assumed that tumour-specific immune T lymphocytes, when they are present, only occur at low frequency among the lymphocytes, because the antigenicity and immunogenicity of tumour antigens is generally only weak. In an animal model studied the frequency of such cells is only one in 15 000 spleen lymphocytes. These tumours-specific cells are usually not fully activated in tumour-bearing animals, and need additional activation signals.

It was now found that the activation of the immune system can be crucially improved by combining a specific and an unspecific immunogenic component. The specific component in this case is represented by the autologous tumour cells isolated from the resected tumour by mechanical and enzymatical methods. The unspecific component is represented by a virus, in particular Newcastle Disease Virus (NDV), contributing to the activation of an inflammatory reaction. NDV is suited for this purpose, because it is a good activator of interferon, and, according to studies, can activate tumour-specific T cells. Moreover, the virus is also particularily well tolerated.

To prepare the vaccine the virus is incubated with irradiated tumour cells, which leads to adsorption of the virus to the tumour cells. The virus-modified tumour cells are inactivated by irradiation, so they cannot grow out as tumours, and are then used as a vaccine. By immunization with this vaccine, sensitized tumour-specific T cells are meant to be activated selectively in situ, and these cells, circulating in the blood and in the lymph, are to be used for a systemic therapy against micrometastases. After intradermal vaccination with such a vaccine, it is intended in the first place to trigger a cutaneous reaction of the delayed type. This reaction, which is specific for cellular immune reactions, indicates that a specific antigen has been recognized, and has resulted in an inflammatory reaction at the site of the vaccination. This could be confirmed by experiments. Due to the presence of the corresponding antigen, the tumour-specific T cells are to be concentrated at the site of the vaccination, and activated to become cytotoxic T lymphocytes with the help of additional activation signals mediated by the virus. When the activated tumour-specific T cells come back in circulation again, i.e. into the blood and into the lymphatic system, they are able to migrate into the organs, and there they can exert their controlling function by recognizing and removing tumour cells bearing the same tumour-antigen.

An essential advantage of the vaccines and their use for the immunotherapy of metastases according to the present invention is the use of a combination of immunogens with the result that, for one, an autologous tumour antigen is optimally presented, and for the other, a second component is given in an optimum dosage for the stimulation of tumour-specific T lymphocytes. This is done by simulating an immune reaction occurring also under physiological conditions in defence against a viral infection. As compared with other forms of therapy, such as adiuvant chemotherapy or high-dose application of lymphokines (interferons or interleukin II), the specific immunotherapy with the virus-modified tumour vaccines according to the present invention has the advantage of having pronouncedly little side-effects. The use of autologous tumour cells should guarantee that antigenicity and immunogenicity of the tumour material remain optimally preserved. The Newcastle Disease Virus (NDV) preferred as the unspecific viral component shows least neurotropic side-effects as compared to other virus, such as influenza A virus or vaccinia virus, which are also used in immunizations with oncolysates. At the same time NDV, compared to the other virus, is a better activator of interferon. In different experimental models, namely the murine ESb model system, the murine bladder carcinoma of the C57 mouse, and the "3LL Lewis Lung" carcinoma system, the specific immunotherapy with virus-modified tumour vaccines according to the present invention could be tested, and their effectiveness was shown. Meanwhile, first results of clinical studies proving the effectiveness of the vaccine according to the present invention have become available.

According to the published German patent application 3432714 lyophilized tumour material is used, and an enzyme, neuraminidase (VCN) is employed. It is known, however, that lyophilized tumour material has a lower immunogenicity than intact cells, and, moreover, the virus used according to the present invention certainly is a stronger adjuvant than the enzyme, as it has already been shown that a number of immunologically relevant gene products, such as interferon alpha, beta, and tumour necrosis factor alpha, are induced by the virus, while such activities could not be shown for the enzyme. In the murine ESb tumour model system referred to above, comparison of virus-modified tumour cells with neuraminidase-treated cells, each used as stimulating cells to activate tumour-specific T killer cells, has shown that only the virus-modified cells were able to induce a significant increase in cytotoxicity, while the neuraminidase-treated cells behaved just like the untreated cells.

In the clinical studies mentioned above, groups of patients were compared receiving either autologous tumour vaccine (ATV) or ATV virus-modified with NDV. It could be seen that 26 out of 27 patients responded to the vaccination, and that NDV had an amplifying effect on the skin reaction, resulting in doubling the number of patients reacting against their own tumour, and increasing the skin reaction. The published German patent application 29 18 927 shows a pharmaceutical composition for the treatment of carcinomas and a method for its preparation, where the composition contains carcinoma cells attenuated with a cytostatic agent to which the carcinoma cells...are sensitive. Therefore, no immunological adiuvant or immunostimulant is used at all, but living autologous tumour cells treated with cytostatic agents, which obviously have not been inactivated otherwise, are used instead. In principle, with the number of cells applied here there is of course a theoretical risk for tumour cells surviving or resistant to cytostatic agents to grow out and form tumours. It is not evident that immunological host-reactions against the tumour are in fact activated. Presumably, the main advantage of this method according to the published German patent application 29 18 927 would consist in improving afterwards the tolerance to chemotherapy. This, however, cannot be compared with the present invention.

The Newcastle Disease Virus (NDV) is particularily suitable as an unspecific component of the vaccine, as, beside very good expression of virus antigens on the cell membrane, it is also an excellent inducer of interferon. The virus is propagated in hens eggs, and inactivated by radiation prior to inoculation into the patient. The NDV is particularily suitable for use in man. NDV is a paramyxovirus (myxovirus avium multiforme), and it is the cause of atypical chicken pest. The virus is only a very weak pathogen in humans. After infection, only in a few humans a unilateral conjunctivitis develops within one to four days which regresses usually after three to four days, and only rarely after two to three weeks. In 50% of patients preauricular lymphadenitis can occur. Occasionally general illnes with headaches and rise of temperature as in a common cold, as well as tracheitis, pharyngitis, and stomatitis occur. A very rare viral pneumonia heals after five to six days. Affection of the CNS and a hemolytic anemia can occur. In earlier studies with NDV-oncolysates of patients with melanoma no side-effects were observed in the application in humans.

Using it in combination with specific tumour antigens, the effects of NDV on the immune system, and its ability to induce inflammatory signal substances make it possible to prepare a strongly immunogenic vaccine which at first triggers a strong direct immunoreaction against the virus. The activation e.g. of macrophages, killer cells, and T lymphocytes following this immunoreaction, and the secretion of lymphokines induced by this, eventually leads to an indirect activation of tumour-specific T killer cells, for which otherwise the low antigenicity of the native tumour cells would not have been sufficient. This cell-mediated immunoreaction against tumour-specific antigens then can be utilized therapeutically to prevent adhesion and growing of tumour cells, and the growing out of already existing micrometastases after removal of the primary tumour.

To prepare the virus-modified tumour vaccine native NDV is incubated under sterile conditions for one hour with tumour cells inactivated by prior irradiation. Resulting from this are tumour cells bearing the virus adsorbed to their surface. Adsorption of the NDV to the tumour cells can be monitored in random samples of fixed cells by ELISA with anti-NDV antibody. The cells are then cryopreserved in liquid nitrogen until they are used.

For use as a vaccine the NDV-modified tumour cells are thawed, tested for their viability, and irradiated to inactivate the virus. The first vaccination is suitably done 10 days after operation. The vaccination is then repeated twice to three times in weekly intervals. The course of therapy is monitored with different test. This is followed by a clinical reassessment (combined with tests) of the patient according to the general guide-lines for follow-up in clinical studies.

During the course of treatment mainly changes of the immunological status of the patient during and after therapy are measured beside the general clinical data. As comparative values tests before and after operation, and before onset of immunotherapy are used. The examinations and tests comprise the cell-mediated and the humoral immune response. The success of the vaccine can be controlled by determining the recidive-free interval.

With respect to application it can be summarized that it should occur not earlier than one week after surgery at least three times in weekly intervals. Two or three, or more, injections with modified irradiated tumour cells are given as the vaccine, and for testing, i.e. the determination of the DTH reaction, another injection with irradiated, non-modified tumour cells, preferably in a lower dose, is administered.

The best results are obtained when autologous material, i.e. material derived from the tumour removed from the patient, is used for the induction phase, i.e. the first two, three, or four injections.

For maintaining therapy, i.e. for later injections in longer intervals, e.g. every three months, which should be maintained over years, it is also possible to use allogenic material, i.e. material derived from the tumours of third parties.

The invention is further illustrated by the following examples.

EXAMPLE 1

Preparation of Inactivated Colorectal Carcinoma Cells

Autologous tumour cells from colorectal carcinomas were obtained directly from the fresh surgical specimen of a patient. The cells were inactivated by irradiaton with $3 \times 10^4$ rad per $1.3 \times 10^7$ tumour cells so that further proliferation of the cells in the patients is not possible. These cells were used to prepare a vaccine from NDV-modified tumour cells. They are cryopreserved in liquid nitrogen until they are used.

EXAMPLE 2

Preparation of a Vaccine from NDV-Modified Tumour Cells

The separated, irradiated tumour cells ($1.3 \times 10^7$ cells) were incubated under sterile conditions with 160 H.U. NDV in serum free medium. Aliquots of the cells were taken and fixed in certain intervals. Using an ELISA with anti-NDV antibody and an immunoperoxidase detection system adsorption of the virus onto the cell surface was determined. After one hour a sufficient quantity of virus was adsorbed on the cell surface. The virus-modified cells are cryopreserved in liquid nitrogen. The cells were again irradiated with 10,000 rad to inactivate the virus prior to use.

EXAMPLE 3

Vaccination of Patients with NDV-Modified Vaccine

Patients which 10 days previously had been operated for a colorectal carcinoma without metastases in other organs were vaccinated. Prior to surgery, the patients were subjected to a skin test (Merieux) with 6 recall antigens to document their immune status. In total, vaccination with NDV-modified tumour cells was done three or four times in weekly intervals (NDV/tumour cell ratio 1:1).

Occurrence of positive skin reactions of the delayed type (DTH reactions) in the patients was observed as an indication for tumour-specific immunization.

I claim:

1. A tumor-specific immunotherapeutic agent comprising separated tumour cells isolated from human tumours, inactivated by radiation and incubated with NDV-virus under sterile conditions in serum-free medium to produce virus-modified tumour cells.

2. The immunotherapeutic agent according to claim 1, wherein the virus-modified tumour cells are irradiated again prior to application.

3. The immunotherapeutic agent according to claim 1, wherein the tumour cells are isolated from human tumours removed by surgery.

4. The immunotherapeutic agent according to claim 1, wherein the tumour cells are isolated from the tumour resected from the patient to be treated.

5. Method for the preparation of the immunotherapeutic agent according to claim 1, which comprises incubating separated, radiation-inactivated tumour cells with NDV-virus under sterile conditions in serum-free medium, and testing for adsorption of the virus by ELISA on fixed cells.

6. Method according to claim 5, which further comprises resterilizing the immunotherapeutic agent by irradiation after testing and prior to application.

7. Method according to claim 5, which further comprises storing the immunotherapeutic agent between incubation and application under cryogenic conditions.

8. An immunotherapeutic composition for enhancing the immune response of a patient comprising an immunotherapeutically effective amount of the immunotherapeutic agent according to claim 1, and a physiologically acceptable carrier.

9. The immunotherapeutic agent according to claim 2, wherein the tumour cells are isolated from human tumours removed by surgery.

10. The immunotherapeutic agent according to claim 2, wherein the tumour cells are isolated from the tumour resected from the patient to be treated.

11. An immunotherapeutic composition for enhancing the immune response of a patient comprising an immunotherapeutically effective amount of the immunotherapeutic agent according to claim 2 and a physiologically acceptable carrier.

12. An immunotherapeutic composition for enhancing the immune response of a patient comprising an immunotherapeutically effective amount of the immunotherapeutic agent according to claim 3 and a physiologically acceptable carrier.

13. An immunotherapeutic composition for enhancing the immune response of a patient comprising an immunotherapeutically effective amount of the immunotherapeutic agent according to claim 4 and a physiologically acceptable carrier.

14. An immunotherapeutic composition for enhancing the immune response of a patient comprising an immunotherapeutically effective amount of the immunotherapeutic agent according to claim 7 and a physiologically acceptable carrier.

15. An immunotherapeutic composition for enhancing the immune response of a patient comprising an immunotherapeutically effective amount of the immunotherapeutic agent according to claim 10 and a physiologically acceptable carrier.

16. The method of claim 5 wherein the tumour cells are isolated from a human tumour removed by surgery.

17. The method of claim 5 wherein the tumour cells are isolated from a tumour resected from the patient to be treated.

18. The immunotherapeutic agent of claim 1 wherein said tumour is a colorectal carcinoma.

19. The method of claim 5 wherein said tumour is a colorectal carcinoma.

20. An immunotherapeutic composition comprising an immunotherapeutic amount of the immunotherapeutic agent of claim 18 and a physiologically acceptable carrier.

* * * * *